United States Patent [19]
Komi et al.

[11] Patent Number: 5,971,917
[45] Date of Patent: *Oct. 26, 1999

[54] ENDOSCOPE HAVING WASHING PORTS

[75] Inventors: Shuji Komi; Haruo Akiba; Seiki Yamaguchi, all of Omiya, Japan

[73] Assignee: Fuji Photo Optical Co., Ltd., Saitama, Japan

[ * ] Notice: This patent is subject to a terminal disclaimer.

[21] Appl. No.: 09/021,020

[22] Filed: Feb. 9, 1998

[30] Foreign Application Priority Data

| Feb. 26, 1997 | [JP] | Japan | 9-060054 |
| Mar. 3, 1997 | [JP] | Japan | 9-065435 |
| Mar. 3, 1997 | [JP] | Japan | 9-065438 |
| Mar. 28, 1997 | [JP] | Japan | 9-094664 |

[51] Int. Cl.$^6$ ................................. A61B 1/015
[52] U.S. Cl. .................. 600/159; 600/156; 600/154
[58] Field of Search ................. 600/121, 123, 600/153, 154, 155, 156, 158, 157, 159

[56] References Cited

U.S. PATENT DOCUMENTS

| 5,447,148 | 9/1995 | Oneda et al. | 600/131 |
| 5,695,450 | 12/1997 | Yabe et al. | 600/156 X |
| 5,810,718 | 9/1998 | Akiba et al. | 600/156 X |

Primary Examiner—John P. Leubecker
Attorney, Agent, or Firm—Snider & Chao LLP; Ronald R. Snider

[57] ABSTRACT

An endoscope which allows a washing brush from an endoscope control section into all tubes, thereby facilitating washing works. In the endoscope control section, a water feeding pipe, for example, is separated into a front tube and a rear tube, and their openings are exposed as washing ports. A support portion of a tube unit is disposed so as to be attachable and detachable to and from the openings of these tubes, and a rear aspirating tube is disposed in the tube unit. This configuration makes it possible to detach and brush the tubes with a washing brush inserted from the openings into the front tubes on the side of a tip section and the rear tubes on the side of a cable. Further, control switches for opening and closing the tubes can be disposed on the tube unit, and elastic tube members may be disposed between the tubes on the side of the tube unit and the tubes on the side of the control section. Furthermore, the tube unit may be made of elastic rubber as a whole.

11 Claims, 14 Drawing Sheets

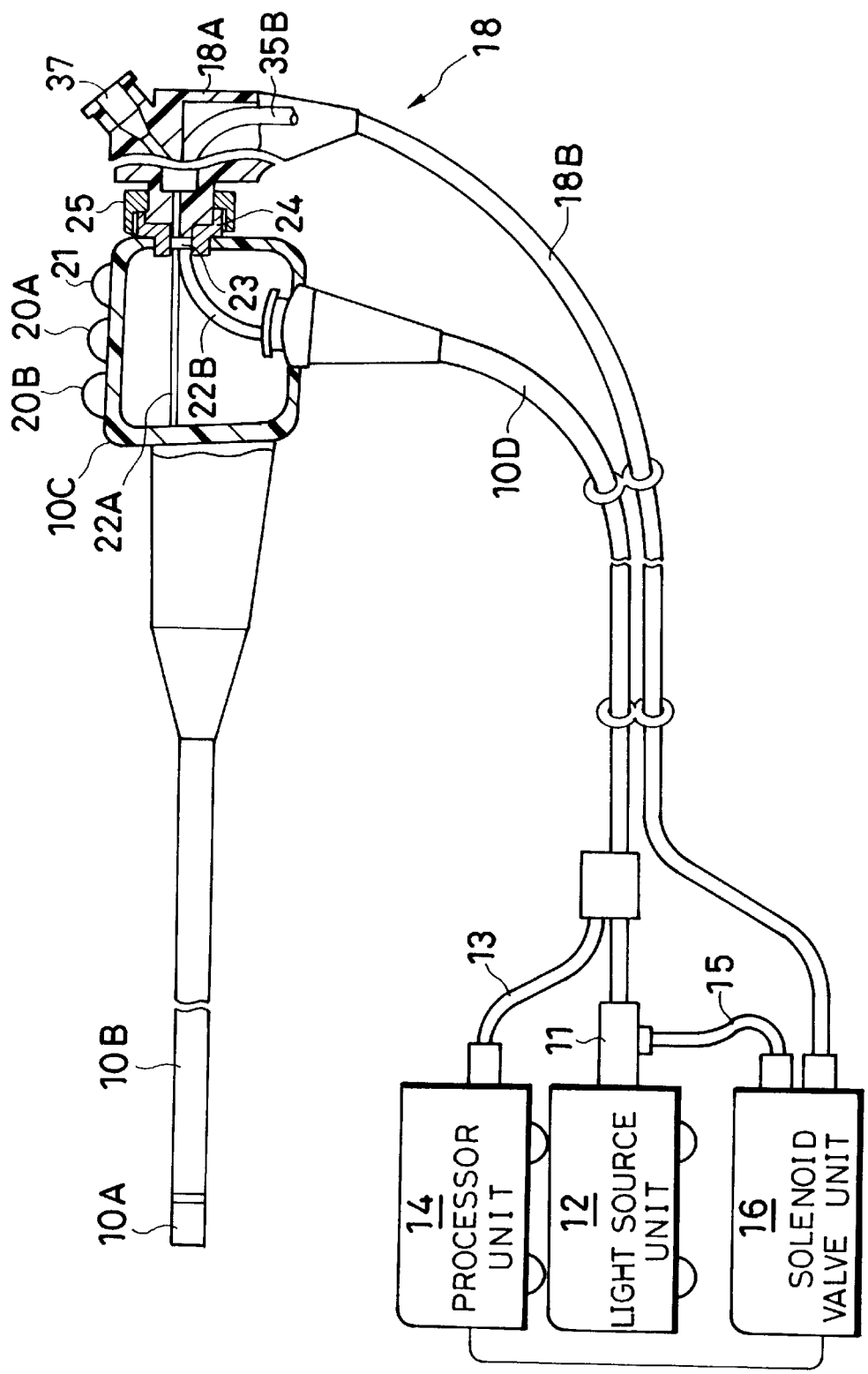

ENDOSCOPE HAVING WASHING PORTS

BACKGROUND OF THE INVENTION

This application claims the priority of Japanese Patent Applications Nos. 9-65438 and 9-65435 filed on Mar. 3, 1997, and No. 9-60054 filed on Feb. 26, 1997, and No. 9-94664 filed on Mar. 28, 1997, which are incorporated herein by reference.

1. Field of the Invention

The present invention has been achieved for facilitating to wash tubes such as air feeding tubes, water feeding tubes and aspirating tubes disposed in endoscopes, and relates to an endoscope which has washing ports formed in a control section.

2. Description of the Prior Art

FIG. 23 schematically shows a conventional electronic endoscope (scope) portion 1 which is composed of a tip section 1A comprising a CCD (charge coupled device), an insert section 1B, a control section 1C and a cable 1D whose end is to be connected to a light source unit and a processor unit for image processing. Disposed on the control section 1C are an angle knob 3, an aspiration button (mechanical switching valve) 4A and an air/water feeding button 4B and a forceps port 5 which used for inserting treating implements toward the tip section to bend a tip section 1A.

Disposed in such an endoscope are an aspirating tube which is a treating tool inserting channel communicated with the forceps port 5 and serves for aspiration, an air feeding tube and a water feeding tube for feeding air and water to the tip section 1A, and so on.

The endoscope which is configured as described above illuminate an interior of a body to be observed with rays which are emitted from the light source unit and transmitted through a light guide and the tip section 1A, and the CCD picks up and observes an image of the interior of the body. During the image pickup and observation, the endoscope allows to feed air and water from the tip section 1A to an observation window, etc. through the air feeding tube and the water feeding tube by manipulating the air/water feeding button 4B, and insert treating implements and aspirate or discharge soiled matters, etc. out of the body through the aspirating tube.

However, the endoscope poses a problem that it does not permit performing efficient washing and disinfection though the endoscope is used in sites of medical treatments and requires to wash and disinfect the tubes. Speaking concretely, the tubes are washed using a brush, but it is difficult to pass the brush at a stroke from the tip section 1A to a tube connector at an end of the cable 1D. The washing brush cannot be inserted deep because the endoscope is long as a whole, and the tubes have remarkably bent parts in the control section 1C and are complicated (partially cut) in a mechanical control section when they are mechanically opened and closed with the aspiration button 4A and the air/water feeding button 4B.

Accordingly, it is conventionally required to flow washing water for a long time, perform tedious washing works and complicate a structure of each section though measures are taken to improve the switching valves so as to allow a washing brush to be inserted as deep as possible.

BRIEF SUMMARY OF THE INVENTION

The present invention has been achieved in view of the problem described above and has a primary object to provide an endoscope which allows a washing brush to be inserted from a control section into all tubes, thereby facilitating washing works with a washing brush.

For accomplishing the object described above, the endoscope having washing ports according to the present invention is characterized in that it is composed of an endoscope main unit in which openings are formed in the course of tubes disposed in the endoscope and exposed outside, and an attachment which serves as stoppers for the openings in the main unit and allows tubes to be connected to these openings.

Speaking in more details, the endoscope having washing ports according to the present invention can be composed, for example, by disposing front tubes from a tip section to a control section, rear tubes from the control section through a cable to a tube control unit (solenoid valve unit), openings of the front and rear tubes formed on an outer circumference of the control section so as to be exposable, returning sections coupled with the openings of the tubes so as to form returning spaces for flow paths, and an attachment which is attachable and detachable to and from the openings in the control section or the returning sections, maintains the returning sections in its attached condition and expose the openings of the front and rear tubes in its detached condition.

The configuration described above allows the openings of the front and rear tubes to be exposed by detaching the attachment from the control section, thereby making it possible to wash the tubes by inserting a washing brush through the openings formed as washing ports separately into the front tubes on a side of the tip section of the endoscope and the rear tubes on a side of the cable. After completing washing, the returning sections can be formed and a communicating function of each tube can be maintained by closing the openings with the attachment.

In the configuration described above, it is possible to dispose an air feeding tube and a water feeding tube as the front and rear tubes, dispose an aspirating tube which also serves as a treating tool inserting channel in a tube unit for leading the tube to a tube control unit through a path separate from the cable, and configure the tube unit so as to have a function of the attachment. This configuration provides a merit that it allows the aspirating tube which aspirate soiled liquid, etc. and the other tubes can be handled separately.

Further, it is possible to branch each tube into two in the endoscope main unit and form an opening as a washing port at a confluence portion of the two branches so that a washing brush can be inserted through this washing port into each of the two tubes. Such a configuration makes it possible to insert a washing brush into tubes through the branched portion after detaching the attachment and maintain a communicating function of each tube for the aspiration, water feeding or water feeding by closing the opening with a stopper member of the attachment.

Further, it is possible to dispose an aspirating tube which serves also as a treating implement insertion channel in the endoscope main unit and form a forceps port so as to communicate with the aspirating tube.

According to another invention wherein a tube unit is disposed separably from an endoscope main unit, it is possible to use control switches for executing opening and closing operations of tubes with a tube control unit (solenoid valve unit). In this case, it is possible to dispose first control switches for opening and closing the tubes on the endoscope main unit, and additionally dispose second controls switches for the similar operations on the tube unit.

The configuration described above provides merits that the tube unit and the solenoid valve unit can be handled separately from other units, and that the switches which are more convenient for the operations are selectable during use of the endoscope.

Still another invention is characterized in that an embodiment comprises an endoscope main unit in which openings are formed as washing ports in the course of tubes disposed in an endoscope and exposed outside, a tube unit which is detachable and attachable to and from the main unit and has tubes connectable to the tubes in the main unit, and elastic tube members which are interposed between the tubes on the side of the main unit and the tubes on the side of the tube unit, and has coupling tubes for coupling these tubes.

The elastic tube members have protruding portions which are inserted or disposed through a base into the tubes on the side of the main unit or the tubes on the side of the tube unit and outer circumferences of these protruding portions can be formed as tapered surfaces which are thinner from their roots toward their tips.

Back flow preventive means for fluid can be formed integrally with the coupling tubes of the elastic tube member.

It is possible to adopt a configuration wherein a fixing ring is connected to the elastic tube members and a mounting groove is formed on an outer circumference of a coupling portion on the side of the main unit or the tube unit for disposing the fixing ring.

In the configuration described above, coupling tubes are formed in the elastic tube members so as to correspond to the other tubes and protruding portions (having the coupling tubes) which are thinner toward their tips are formed, for example, at both ends of a collar-like base portion. The tube unit and the main unit are coupled in a condition where the protruding portions are inserted into the tubes on the sides of the main unit and the tube unit, whereby airtight conditions of the tube are favorably maintained. Further, it is sufficient to wash only the tubes when the elastic tube member is configured so as to be easily detachable or disposable after detaching the tube unit.

Further, it is possible to dispose a tube unit in which aspirating tube is disposed as the attachment described above and make this tube unit of an elastic material so that the tube unit is disposable and requires no washing.

BRIEF DESCRIPTION OF THE DRAWINGS

FIG. 6 is a diagram illustrating an overall configuration of the endoscope preferred as the first embodiment;

DETAILED DESCRIPTION OF THE PREFERRED EMBODIMENTS

First Embodiment

Figure 1:
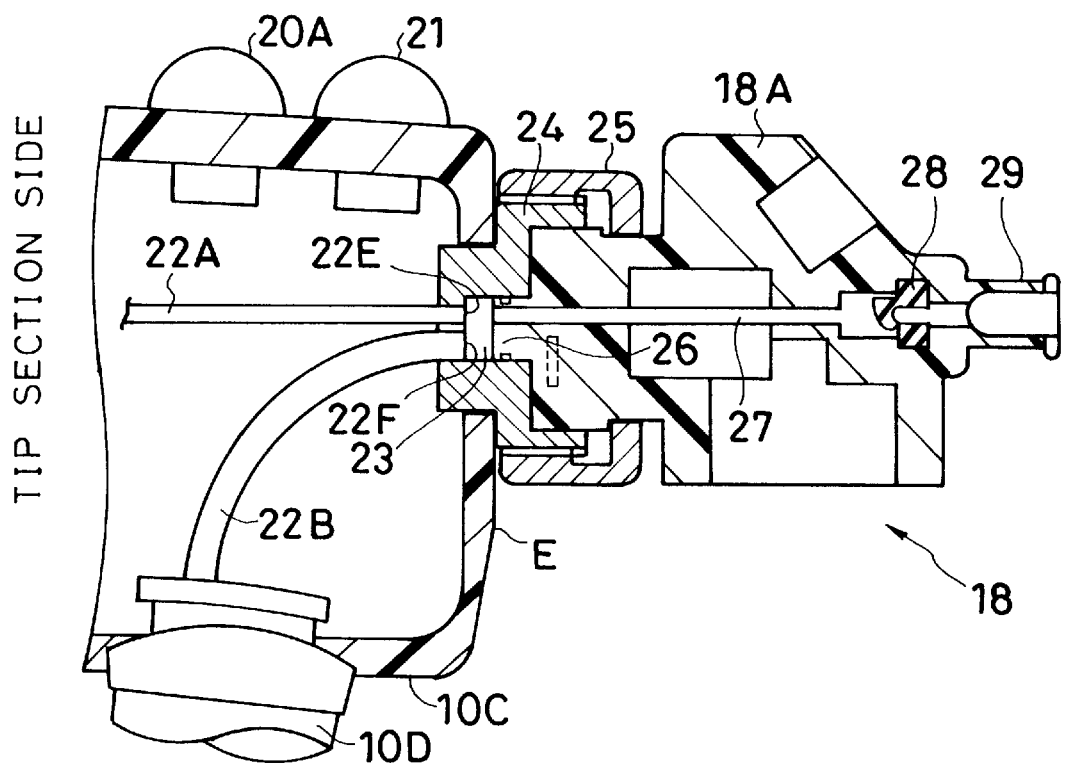
FIG. 1 is a sectional view taken along a I—I line in FIGS. 2(A) and 2(B) for illustrating a structure of a tube (water feeding tube) of an endoscope (control section) preferred as a first embodiment of the present invention.

FIGS. 1 through 6 show a tube structure of an endoscope preferred as the first embodiment of the present invention and description will be made first of an overall configuration of the endoscope. In FIG. 6, an electronic endoscope 10 which is configured as an endoscope consists of a tip section 10A comprising a CCD, an insert section 10B, a control section 10C and a first cable 10D. A connector 11 of the first cable 10D is connected to a light source unit 12 and a signal cable 13 which is branched from the course of the first cable 1D is connected to a processor (image processor) unit 14.

In other words, a light guide is laid from the tip section 10A to the light source unit 12, and a signal line for controlling the CCD and reading out video signals is laid from the tip section 10A to the processor unit 14 on the endoscope 10, thereby enabling to project rays from the tip section 10A and read out the video signals from the CCD.

Further, a tubing cable 15 which is branched from the connector 11 is connected to a solenoid valve unit (tube control unit) 16 which is equipped with a pump, etc., and an air feeding pipe and a water feeding pipe described later are disposed in the tubing cable 15 and the first cable 10D. Furthermore, a tube unit 18 (consisting of a support portion 18A and a second cable 18B) is detachably attached to the control section 10C and an aspirating tube is led to the solenoid valve unit 16 by the tube unit 18. The solenoid valve unit 16 is electrically connected to the processor unit 14.

Figure 23:
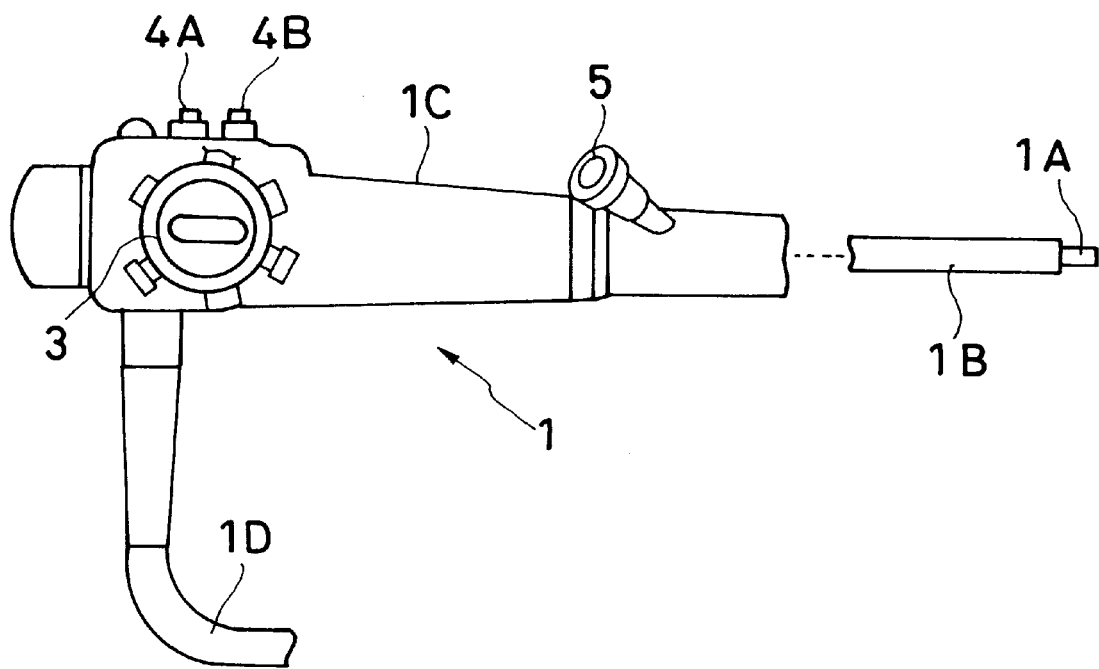
FIG. 23 is a schematic diagram showing a configuration of a conventional endoscope.

An aspiration button (operation switch) 20A, air/water feeding button (two-step switch) 20B and a hard copy button 21 which are electric switches are disposed on the control section 10C, and operation control signals are transmitted from these buttons to the solenoid valve unit 16. In the first embodiment, open/close control of the tubes is performed not with the mechanical switching valves such as those shown in FIG. 23 but with switching (solenoid) valves disposed in the solenoid valve unit 16 which are operated with the electric switches described above.

Figure 2A:
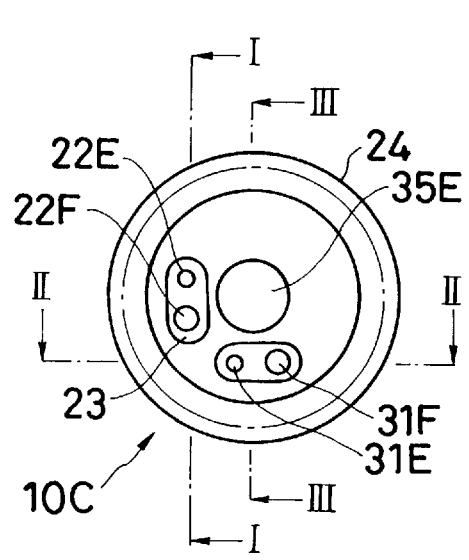
FIG. 2(A) is a diagram illustrating a configuration of a coupler on a side of the control section when the control unit and the tube unit shown in FIG. 1 are detached.
Figure 2B:
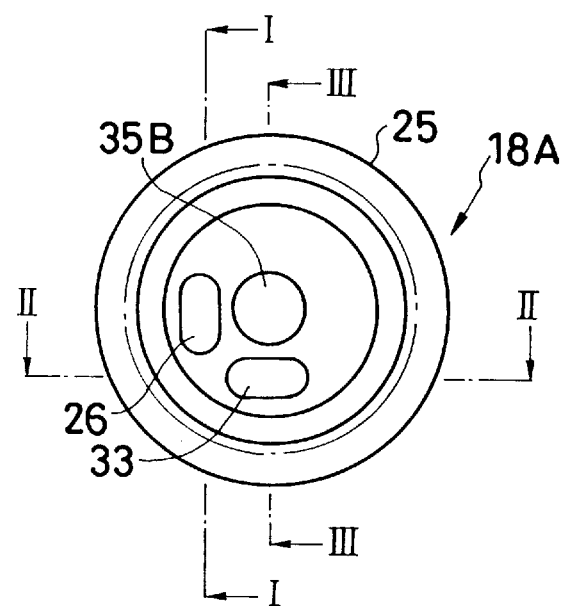
FIG. 2(B) is a diagram illustrating a configuration of a coupler on a side of the tube unit when the control section and the tube unit shown in FIG. 1 are detached.

FIG. 1 shows a structure related to the water feeding pipe in a sectional view taken along a I—I line in FIGS. 2(A) and 2(B). In the control section 10C, the water feeding tube is separated into a front water feeding tube 22A which is disposed from a side of a tip toward a rear end surface E and a rear water feeding tube 22B which is disposed from the rear end E to a side of the first cable 10D as shown in FIG. 1. Openings 22E and 22F of these front and rear water feeding tubes 22A and 22B are disposed in a returning section 23 which is formed on the rear end surface E. (This returning section 23 may be formed on a side of the tube unit.)

To couple the support portion (attachment) 18A of the tube unit 18 detachably with the rear end surface of the control section 10C, there is disposed, as a receptacle for the support portion 18A, a cylindrical receiving portion 24 in which a male thread is formed on an outer circumference, openings 22E and 22F of the water feeding pipes 22A and 22B are disposed and a returning section 23 having a predetermined space is reserved as shown in FIG. 2(A).

On the other hand, a control ring 25 which has tapping on an inner circumference thereof and is rotatably is disposed on the support portion 18A and the tube unit 18 is attached to the operation section 10C by screwing the control ring over the receiving portion 24. A stopper member (convex portion) 26 which has a form to fit into a portion of the returning section 23 is formed inside the control ring 25 of the support portion 18A as shown in FIG. 2(B) and a gasket or a similar member is fitted over the stopper member 26.

Further, a lens surface washing port 29 is disposed in the support portion 18A by way of a connecting tube 27 and a back flow preventive valve 28 as shown in FIG. 1. This lens surface washing port 29 is a supply port for injecting water or the like as a splash to a lens surface of an observation window of the tip section 10A.

Figure 3:
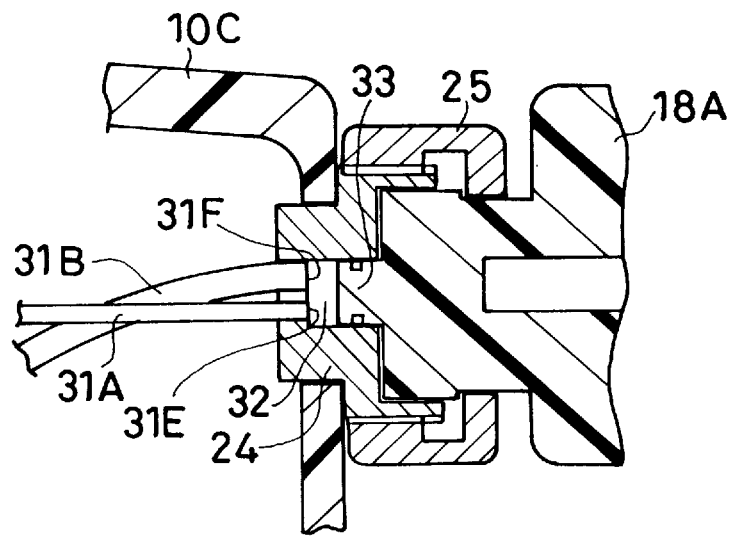
FIG. 3 is a sectional view taken along a II—II line in FIGS. 2(A) and 2(B) for illustrating a structure of an air feeding tube used in the first embodiment.

FIG. 3 shows a structure related to the air feeding pipe in a sectional view taken along a II—II line in FIGS. 2(A) and 2(B). In this structure also, the air feeding tube is separated into a front air feeding tube 31A and a rear air feeding pipe 31B, and openings 31E and 31F are disposed in a returning section 32. A stopper member 33 which fits into the returning section 32 while reserving a flow path returning space is disposed on a side of the support portion 18A.

Figure 4:
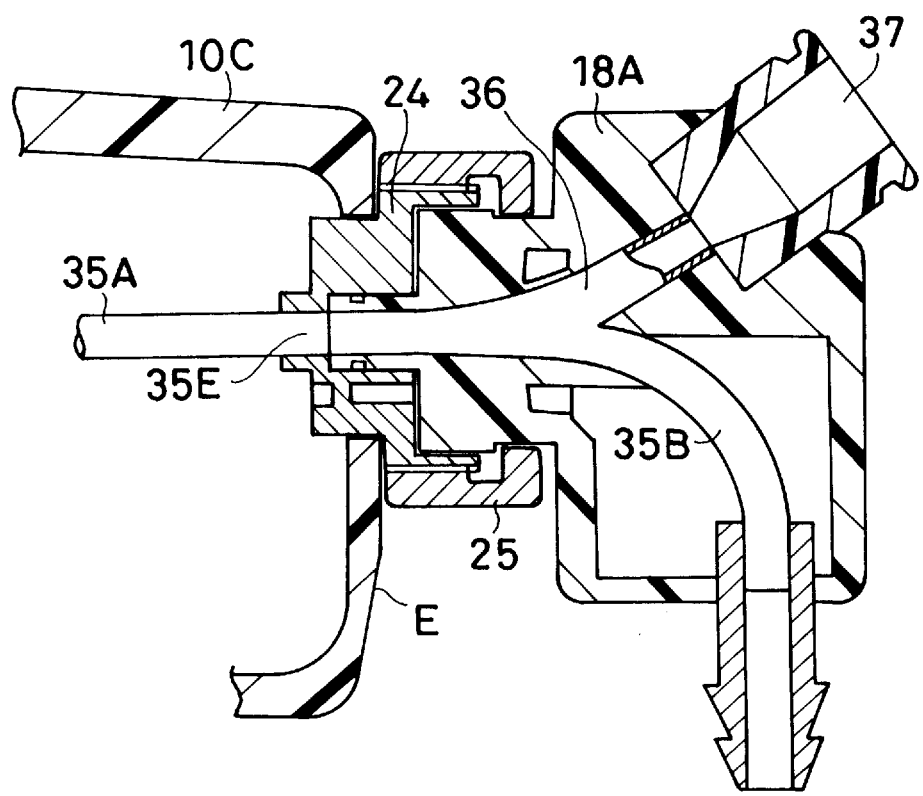
FIG. 4 is a sectional view taken along a III—III line in FIGS. 2(A) and 2(B) for illustrating a structure of an aspirating tube in the first embodiment.

FIG. 4 shows a structure related to the aspirating tube in a sectional view taken along a III—III line in FIGS. 2(A) and 2(B). In the first embodiment, an aspirating tube is disposed in a separate path. Speaking concretely, a front aspirating tube 35A is disposed in the control section 10C and an opening 35E is disposed at the center of the receiving portion 24, whereas a rear aspirating tube 35B is disposed on the side of the tube unit 18. A forceps port 37 is disposed in the support portion 18A of the tube unit 18 by way of a branch tube 36 and a stopper cap (not shown) is fitted over the forceps port 37. Accordingly, the aspirating tube 35 performs a role to aspirate water and the like out of a body to be observed and also serves as a treating implement insertion channel for introducing treating implements such as forceps.

In the first embodiment which is configured as described above, the tube unit 18 is coupled with the control section 10C by screwing the control ring 25 over the receiving portion 24 as shown in FIG. 1 before using the endoscope. In this condition, an aspirating operation and an air/water feeding operation can be carried out by manipulating the aspiration button 20A and the air/water feeding button 20B. In other words, a control circuit in the solenoid valve unit 16 operates the pump and performs switching control of corresponding solenoid valves when operation control signals of the aspirating button 18A are transmitted from the aspiration button 20A and the air/water feeding button 20B to the solenoid valve unit 16 by way of the processor unit shown in FIG. 6.

Soiled water and the like is aspirated out of the body to be observed by way of the aspirating tubes 35A and 35B, and accommodated from the tube unit 18 into a tank or a similar member when the aspiration button 20A is manipulated, whereas air is fed by way of the rear air feeding tube 31B, the returning section 32 and the front air feeding tube 31A or water is fed by way of the rear water feeding tube 22B, the returning section 23 and the front water feeding tube 22A when the air/water feeding button 20B is manipulated. Further, the observation window lens can be washed during use of the endoscope by injecting water with a syringe or the like through the lens surface washing port 29 of the tube unit 18. Various medical treatments can be carried out with treating implements inserted from the forceps port 37 through the front aspirating tube 35A.

Figure 5A:
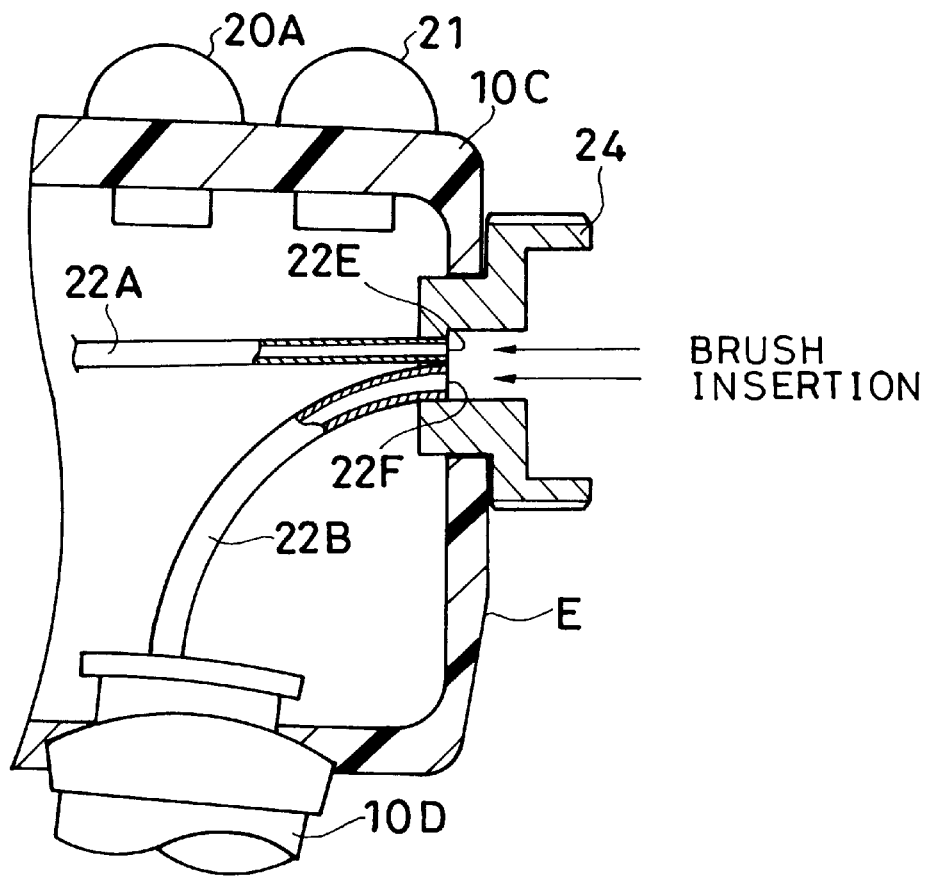
FIG. 5(A) is a diagram illustrating the control section in a condition where the tube unit is detached from the control section in FIG. 1.

For washing the tubes after completing use of the endoscope, a washing brush can be inserted from the side of the rear end surface E of the control unit 10C as shown in FIG. 5(A) after detaching the tube unit 18 from the receiving portion 24 of the control section 10C by unscrewing the control ring 25. All the tubes of the endoscope can be brushed with the washing brush inserted sequentially from the openings 22E and 22F of the front and rear water feeding tubes 22A and 22B, from the openings 31E and 31F of the front and rear air feeding tubes 31A and 31B, and from the opening 35E of the aspirating tube 35A as shown in FIG. 2(A).

Figure 5B:
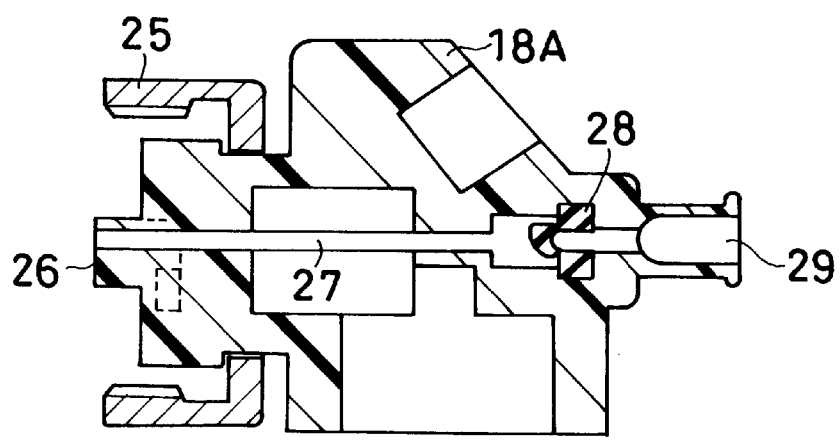
FIG. 5(B) is a diagram illustrating a support portion for the tube unit in a condition where it is detached from the control section.

In addition, the connecting tube 27, the aspirating tube 35B, the branch tube 36 and so on the side of the tube unit 18 which are shown in FIG. 5(B) are also brushed.

Figure 7:
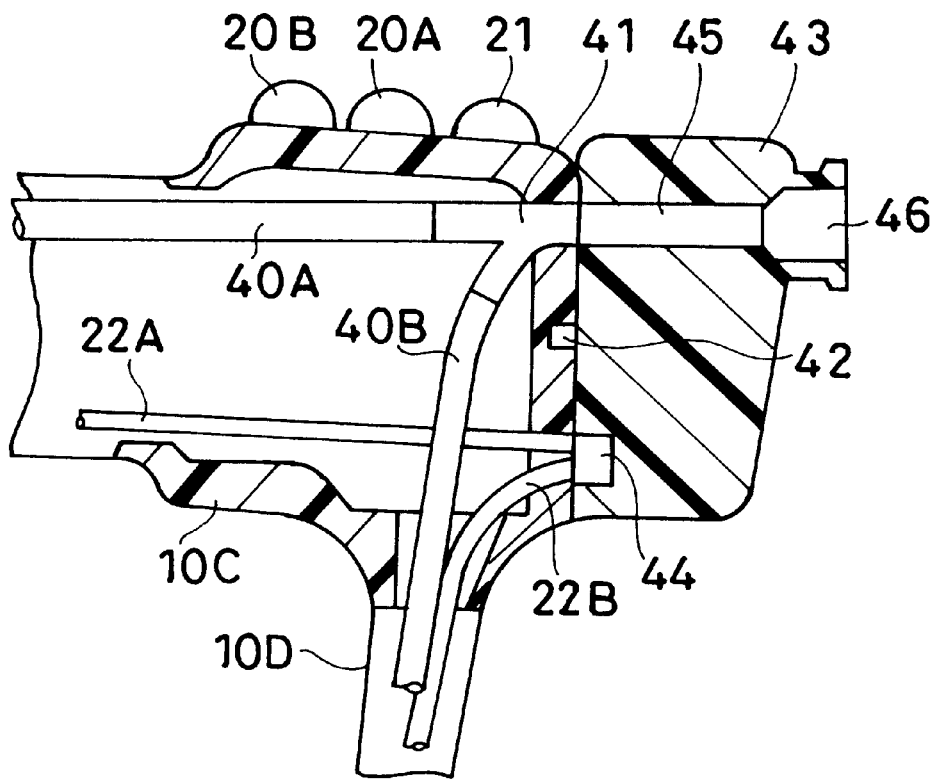
FIG. 7 is a diagram illustrating a structure of a second embodiment of the present invention.
Figure 8:
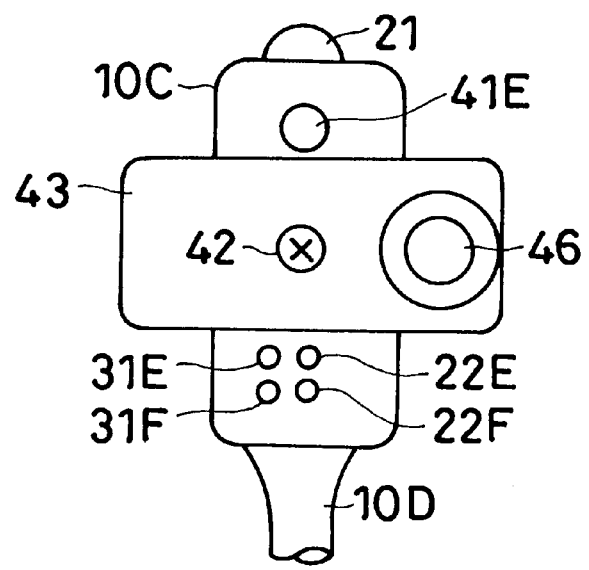
FIG. 8 is a diagram of the control section as seen from its rear end.

Second Embodiment FIGS. 7 and 8 show a second embodiment wherein no tube unit is disposed in a tube structure. In the second embodiment, water feeding tubes 22A, 22B and air feeding tubes are disposed similarly, whereas aspirating tubes 40A and 40B are connected with a branch tube 41. Attached to a rear end surface of a control section 10C is an attachment 43 which rotates around a shaft 42 and in which a returning section 44 for the water feeding tubes 22A and 22B is arranged, and a forceps port 46 is disposed by way of a connecting tube 45.

The second embodiment which, as shown in FIG. 8, is configured as described above makes it possible to easily expose openings 22E, 22F of the water feeding tubes 22A, 22B, openings 31E, 31F of the air feeding tubes and an opening 41E of the aspirating tube 40A. The tubes can be washed with a washing brush inserted from the opening 22E and so on.

Though the aspirating tubes 35, 40 are structured differently from the air feeding tube 22 and the water feeding tube 31 in each of the embodiments described above, it is possible to dispose the aspirating tube similarly to the air feeding tube and the water feeding tube.

As apparent from the foregoing description, the front tubes on the side of the tip of the endoscope and the rear tubes on a side of a cable can be brushed from the openings formed as washing ports, or all the tubes can easily be washed with a washing brush after the attachment is detached. When a tube unit is disposed only for the aspirating tube, it is possible to handle the aspirating tube which aspirate soiled liquids, etc. separately from the other tubes. The tube unit can be subjected, for example, to a sterilizing treatment using an autoclave or the like for efficient washing works.

Third Embodiment

FIGS. 9 through 13 show a configuration of a third embodiment. An aspiration button 58A, an air/water feeding button 58B and a hard copy button 59 are mounted on a control section 10C shown in FIGS. 9 and 10, an aspirating tube 61, a water feeding tube 61 and an air feeding tube 63 (shown in FIG. 12) are arranged toward a rear end surface E in the control section 10C. Each of the tubes 61, 62 and 63 has a portion 61A, 62A or 63A which is branched into two on a side of the rear end surface of the control section 10C.

Figure 11:
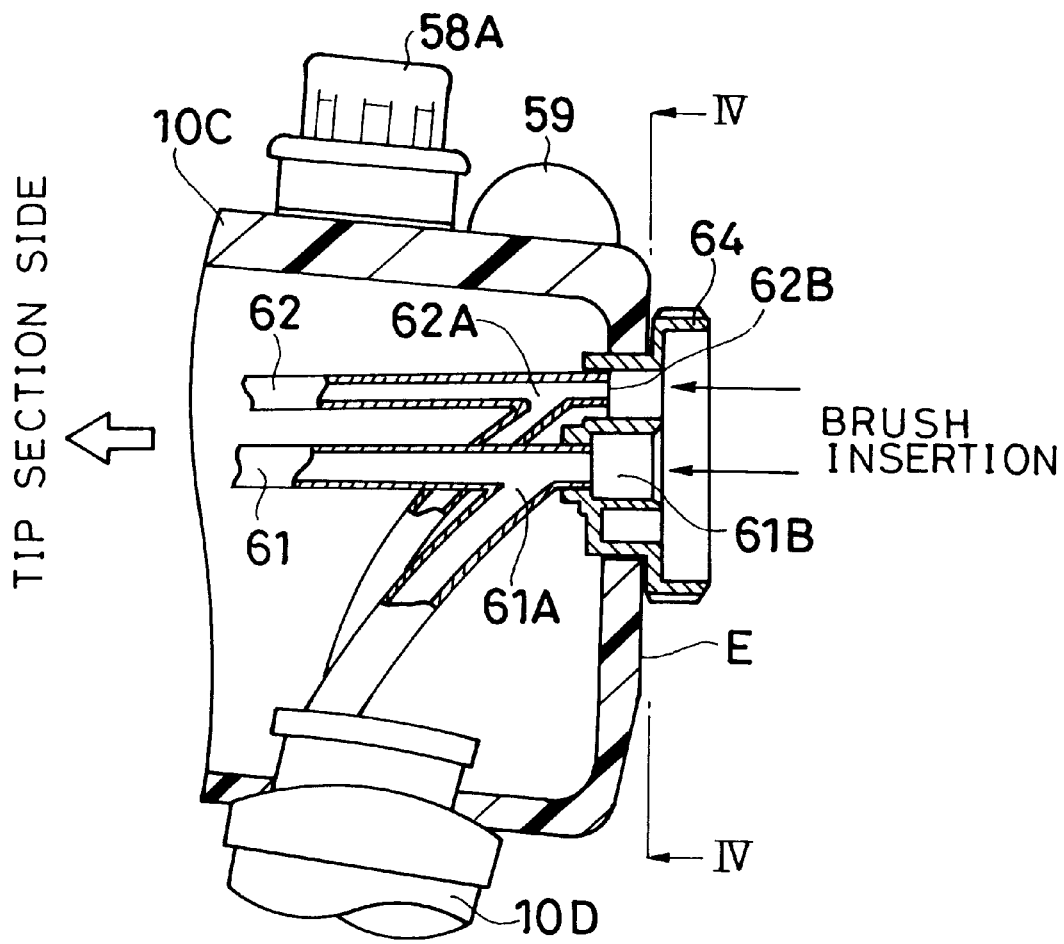
FIG. 11 is a diagram of the control section shown in FIG. 9 from which an attachment is detached.
Figure 12:
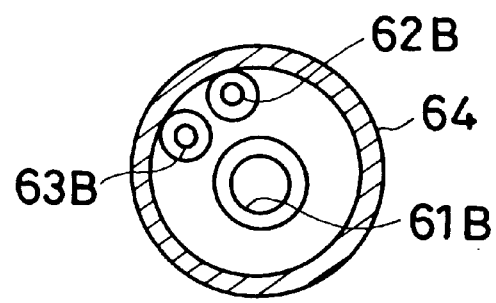
FIG. 12 is a sectional view taken along a IV—IV line in FIG. 9 for illustrating a tube coupler.

As a receptacle for a coupler, a cylindrical receiving portion 64 which has a male thread on an outer circumference thereof is disposed on the rear surface of the control section 10C as shown in FIG. 11, and openings of the tubes 61, 62 and 63 are disposed in this receiving portion 64. Speaking concretely, an opening 61B of the aspirating tube 61 (having a connecting tube), an opening 62B of the water feeding tube 62 and an opening 63B of the air feeding tube 63 are arranged collectively in the cylinder of the receiving portion 64 as shown in FIG. 12.

Figure 9:
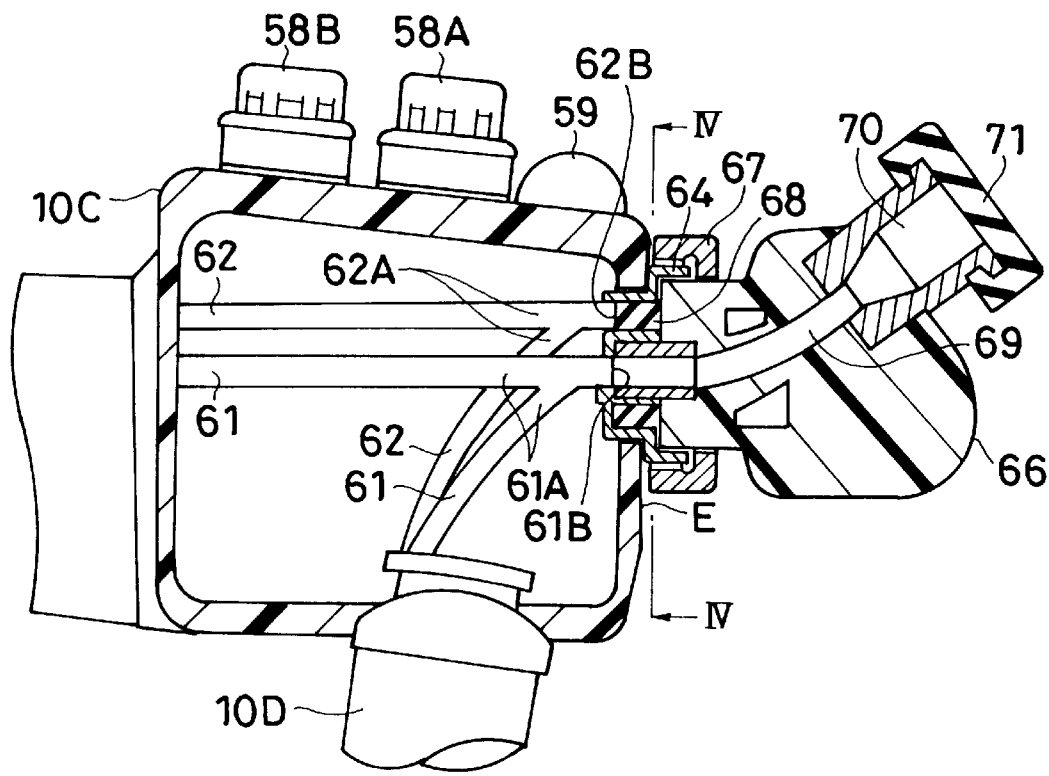
FIG. 9 is a partial sectional view illustrating a tube structure of a control section of an endoscope preferred as a third embodiment of the present invention.
Figure 10:
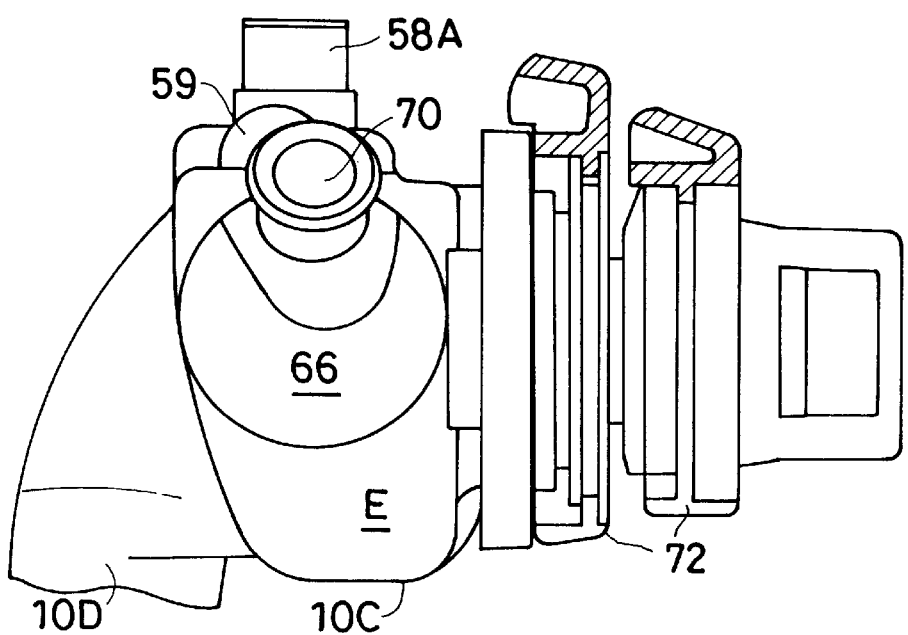
FIG. 10 is a diagram of the control section shown in FIG. 9 as seen from its rear end.
Figure 13:
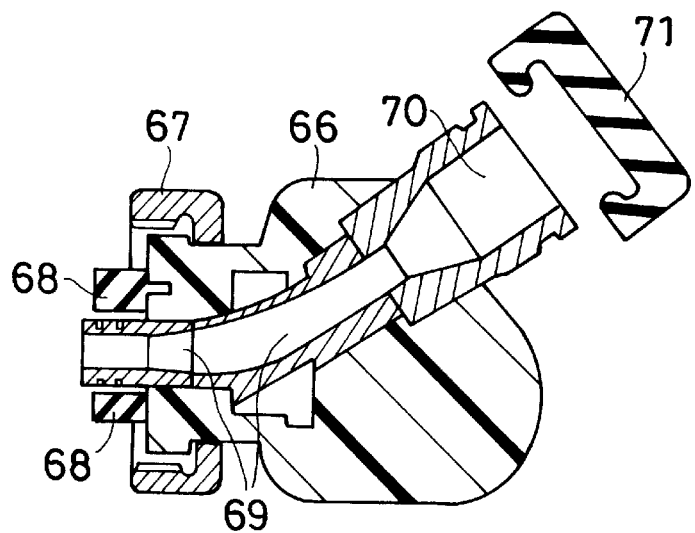
FIG. 13 is a diagram illustrating the attachment which is detached from the control section in the third embodiment.

On the other hand, there is disposed an attachment 66 which has stopper members for closing the openings 61B through 63B of the tubes 61 through 63 as shown in FIGS. 9 and 13. A control ring 67 which has a tapped inner circumference is rotatably disposed as a control member for the coupler and stopper gaskets (stopper members) 68 for closing the opening 62B of the water feeding tube 62 and the opening 63B of the air feeding tube 63 are disposed in the attachment 66.

A forceps port 70 is disposed in the aspirating tube 61 by way of a connecting tube 69 and a stopper cap 71 is fitted over the forceps port 70. Accordingly, the aspirating tube 61 performs a role to aspirate water and so on out of a body to be observed and serves also as a treating implement insertion channel for introducing treating implements such as forceps. In addition, an angle knob 72 which is used for bending a tip section 10A is mounted on the control section 10C.

In the third embodiment which is configured as described above, the attachment 66 is coupled with the control section 10C by screwing the control ring 67 over the receiving portion 64 as shown in FIG. 9 before using the endoscope. In this condition, an aspirating operation and air/water feeding operation can be carried out by manipulating the aspiration button 58A and the air/water feeding button 58B.

In other words, a control circuit in a solenoid valve unit 16 operates a pump and performs switching operations of corresponding solenoid valves when operation control signals are transmitted from the aspiration button 58A, etc. through a processor unit to the solenoid valve unit 16.

Accordingly, soiled water and the like are aspirated out of a body to be observed through the aspirating tube 61 when the aspiration button 58A is manipulated, whereas air is fed to a tip section 10A through the air feeding tube 63 or water is fed to the tip section 10A through the water feeding tube 62 when the air/water feeding button 58B is manipulated. Further, various kinds of medical treatment can be carried out with treating implements inserted from the forceps port 70 through the aspirating tube 61 after removing the stopper cap 71.

For washing the tubes after completing use of the endoscope, on the other hand, a washing brush can be inserted from each of the openings 61B through 63B as shown in FIG. 11 after detaching the attachment 66 from the receiving portion of the control section 10C by unscrewing the control ring 67. At this stage, all the tubes of the endoscope can be brushed by inserting the washing brush sequentially into the tubes 61 through 63 on the side of the insert section 10B and the tip section 10A which are branched from the branch portions 61A and 62AA (63A), and the tubes 61 through 63 on the side of a cable 10D. Needless to say, the connecting tube 69 and so on which are disposed on the side of the attachment 66 are also brushed.

As apparent from the foregoing description, the third embodiment also makes it possible to brush the tubes on the side of the tip section of the endoscope and the tubes on the side of a cable and facilitates to wash all the tubes with a washing brush.

Fourth Embodiment

Figure 14:
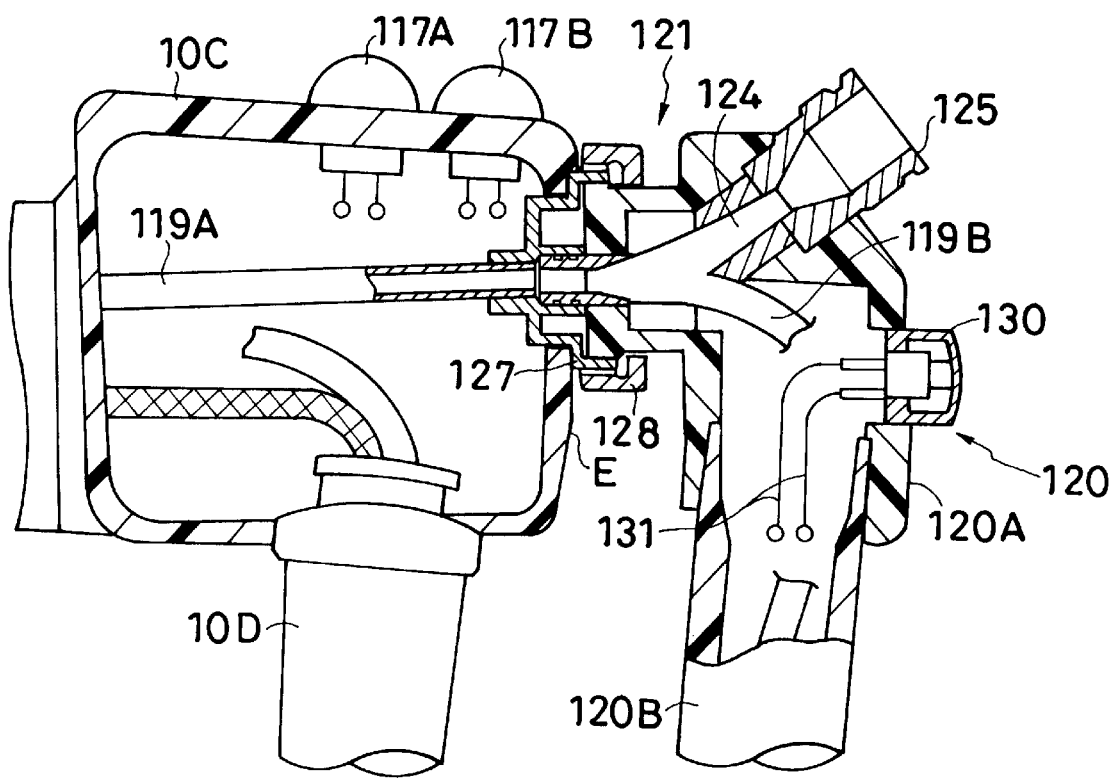
FIG. 14 is a sectional view illustrating a configuration of an endoscope (first coupler) preferred as a fourth embodiment of the present invention.
Figure 15:
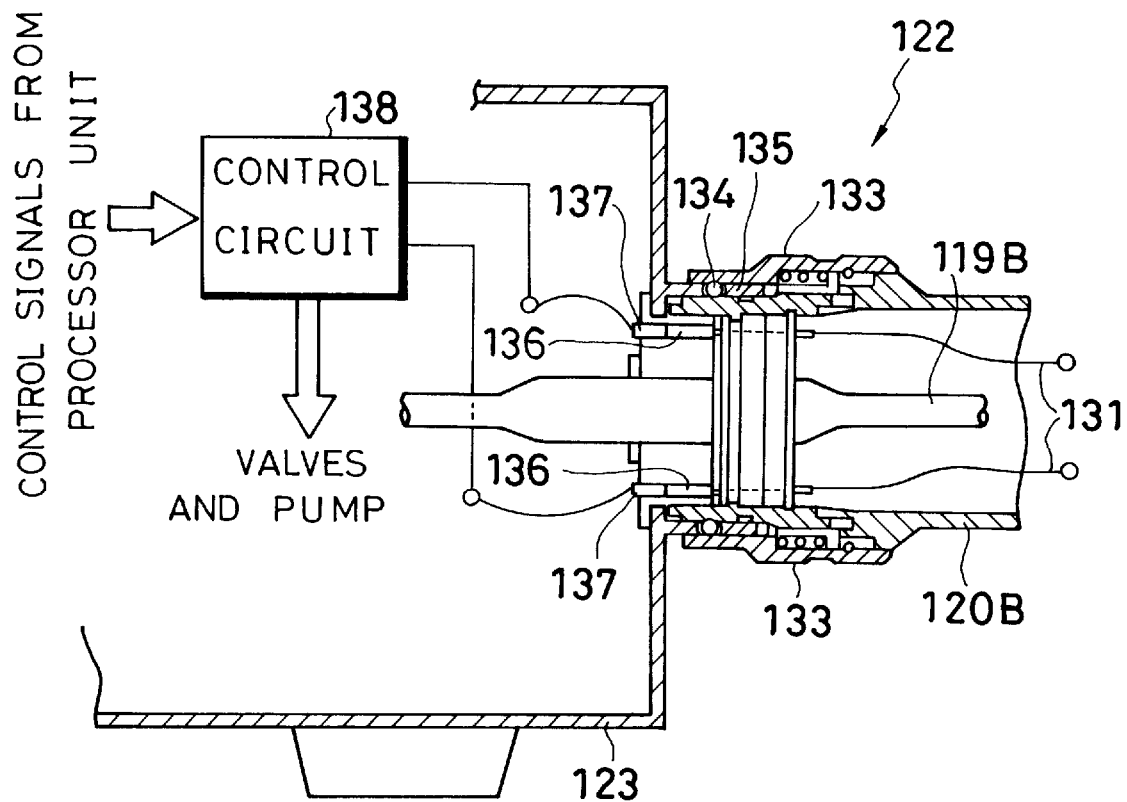
FIG. 15 is a diagram illustrating a configuration of a solenoid valve unit (second coupler) used in the fourth embodiment.

FIGS. 14 and 15 show a configuration of an endoscope preferred as a fourth embodiment of the present invention. In FIG. 14, a first aspiration button 117A and a hard copy button 117B which are electric switches are disposed on a control section 10C, and an aspirating tube 119A is arranged in the control section 10C. No air feeding tube or water feeding tube is arranged in the fourth embodiment.

A tube unit 120 is detachably attached to a rear end E of the control section 10C with a first coupler (connector) 121 and connected to a solenoid valve unit 123 by way of a second coupler 122 as shown in FIG. 15. The tube unit 120 consists of a support portion 120A and a second cable 120B, an aspirating tube 119B which is to be coupled with an aspirating tube 119A on the side of the control section 10C is disposed in the tube unit 120 and these tubes are led to a solenoid valve unit 123.

The solenoid valve unit 123 is electrically connected to a processor unit 14, receives operating control signals from the first aspiration button 117A, and performs an aspirating operation through the tubes 119A and 119B. The first coupler 121 which is used for connecting the tube unit 120 to the control section 10C is composed of a receiving portion 127 and a control ring 128.

A second aspiration button 130 is disposed under a forceps port 125 on a support portion 120A of the tube unit 120 and connected to the solenoid valve unit 123 by a connecting line 131 through the second cable 120B.

On the second coupler 122 as shown in FIG. 15, on the other hand, a slide control ring 133 is disposed on the side of the second cable 120B and a support cylinder 135 which holds a vertically movable engaging ball 134 is disposed on the side of the solenoid valve unit 123. This configuration allows the tube unit 120 to be attached by sliding the slide control ring 133 so as to engage and disengage the ball 134 with and from a groove formed in a support cylinder on the side of the second cable 120B.

The connecting line 131 of the second aspiration button 130 which passes through the second cable 120B is connected to the solenoid valve unit 123 by way of a pin-like electrode 136 and a cylindrical electrode 137. The solenoid valve unit 123 comprises a control circuit 138 into which controls signals are input from the second aspiration button 130.

Control signals from the first aspiration button 117A are also input into the control circuit 138 by way of a processor unit 14 and the control circuit 138 opens and closes the solenoid valves on the basis of these control signals. Further, the fourth embodiment allows the processor unit 14 or the solenoid valve unit 123 to select effectuation of both or either of the first aspiration button 117A and the second aspiration button 130.

The fourth embodiment which is configured as described above makes it possible to perform an aspirating operation with an aspiration button whichever is more convenient for manipulation when the tube unit 120 is connected to the main unit, and both the first aspiration button 117A and the second aspiration button 130 are effectuated. Further, the fourth embodiment allows only either of the aspiration buttons 117A and 130 to be effectuated.

Even when the tube unit 120 is detached from the main unit and handled together with the solenoid valve unit 123, the fourth embodiment allows the aspirating operation to be executed with the second aspiration button 130.

Fifth Embodiment

Figure 16:
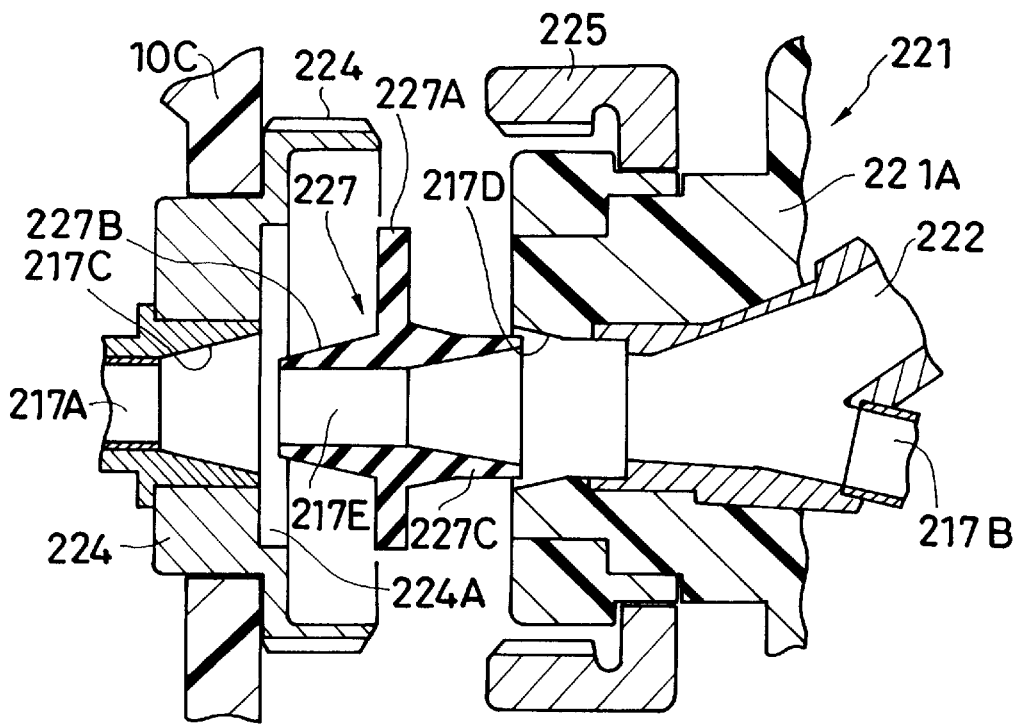
FIG. 16 is a diagram illustrating a coupler of an endoscope preferred as a fifth embodiment of the present invention, or a structural diagram of an aspirating tube.
Figure 17:
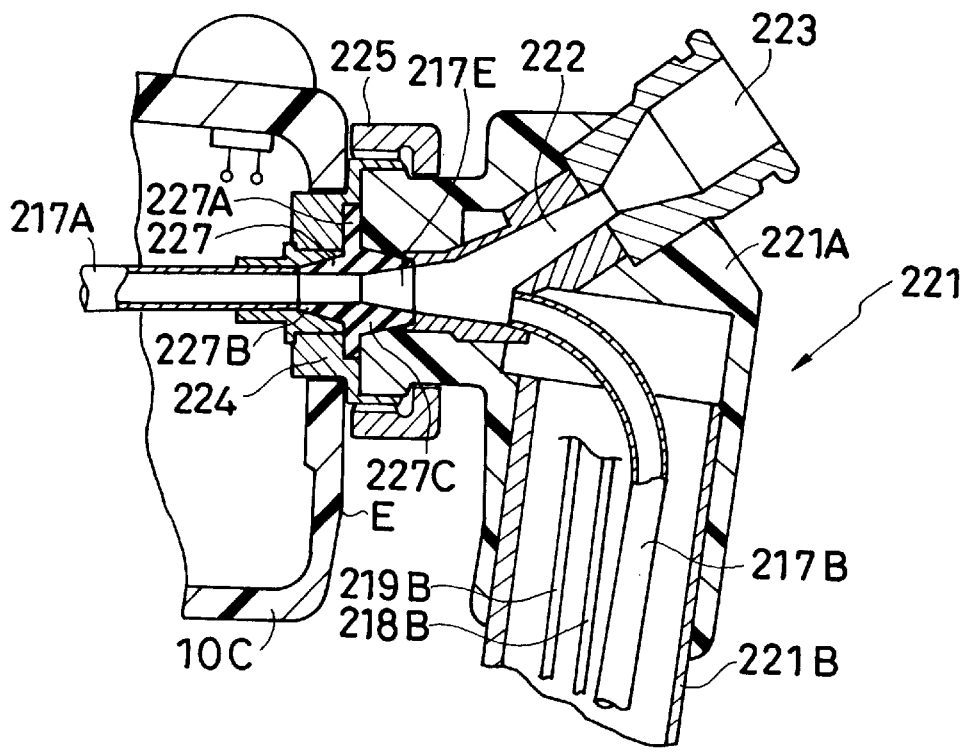
FIG. 17 is a sectional view illustrating the coupler composed by coupling the members shown in FIG. 16.

FIGS. 16 through 19 show a configuration of an endoscope preferred as a fifth embodiment which permits easily maintaining airtightness in a coupler and has favorable washability. FIGS. 16 and 17 show a configuration of an aspirating tube wherein an aspirating tube 217A is disposed nearly at a center of a coupler in a control section 10C of the endoscope.

A tube unit 221 which is detachably attached to a rear end of the control unit 10C is composed of a support portion 221A and a cable 221B, and an aspirating tube 217B which is to be coupled with the aspirating tube 217A and connected to a solenoid valve unit is disposed in the support portion 221A and the cable 221B. A forceps port 223 is disposed in the aspirating tube 217B by way of a branch tube 222. A receptacle 224 which has male thread on an outer circumference thereof is attached to the control section 10C and a control ring 225 which is tapped on its inner circumference and rotatable is fitted over the support portion 221A of the tube unit 221.

Further, an aspirating connector (tube) 217C having a conical inside surface which is tapered so as gradually enlarge an aperture toward an outlet is connected to the aspirating tube 217A in the receptacle 224 and a similar aspirating connector (tube) 217D is connected to the aspirating tube 217B in the support portion 221A. A first elastic tube member 227 is disposed so as to connect the aspirating connectors 217C and 217D to each other.

The first elastic tube member 227 is made of a rubber material, and conical tapered protrusions 227B and 227C having outer circumferences which are thinner toward their tips are formed at both ends of a collar-like (disk-like) base 227A of the first elastic tube member 227, thereby forming an aspirating tube 217E. This base 227A is formed so as to be fitted into a step portion 224A of the receptacle 224, the protrusion 227B is formed so as to be fitted into the aspirating connector 217C and the protrusion 227C is formed so as to be fitted into the aspirating connector 217D. The base 227A has thickness which is slightly larger than a width of the step portion 224A, and the protrusions 227B and 227C have outer circumferences whose diameters are slightly longer than inside diameters of the aspirating connectors 217C and 217D so as to cope with deterioration or contraction of the rubber material.

Figure 18:
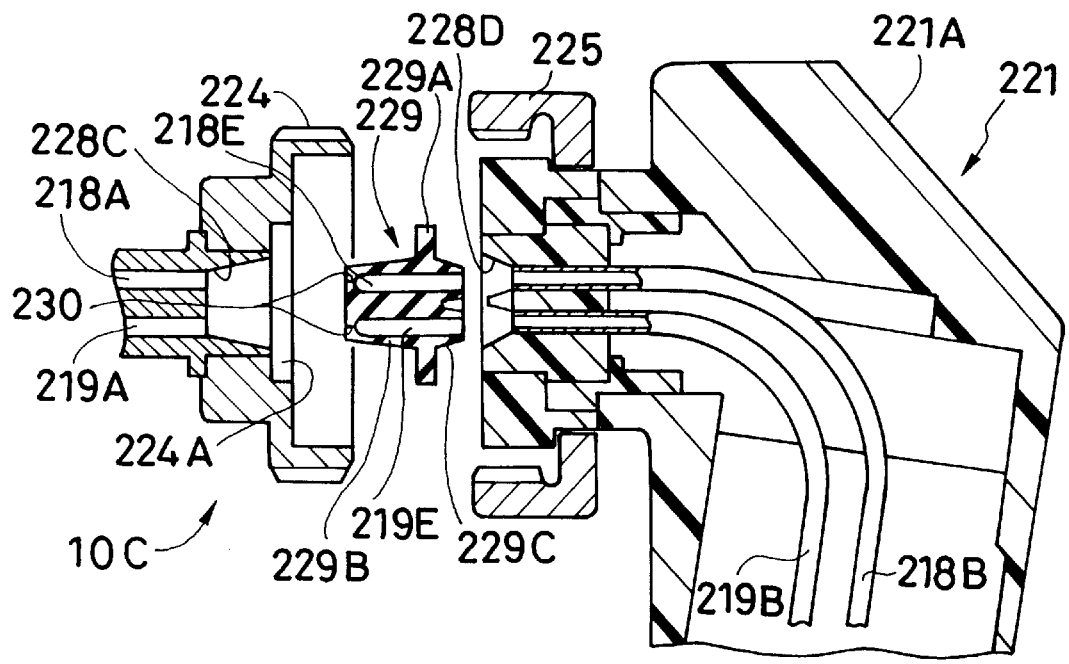
FIG. 18 is a diagram illustrating the coupler of the endoscope preferred as the fifth embodiment, or a structural diagram of an air or water feeding tube.
Figure 19:
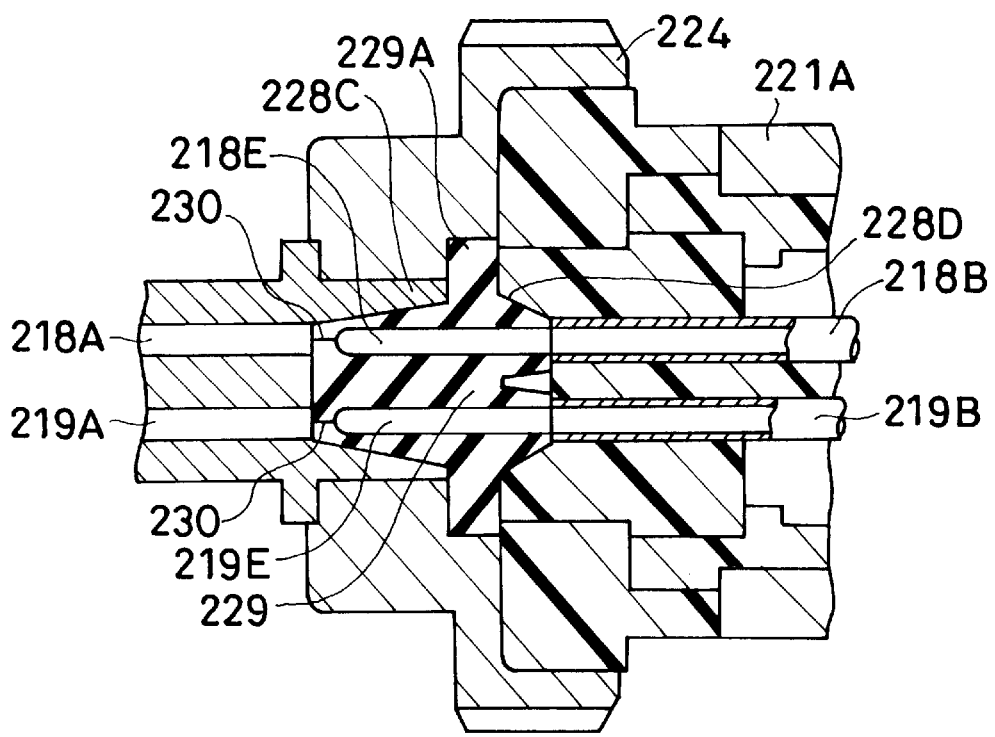
FIG. 19 is a sectional view illustrating the coupler which is composed by coupling the members shown in FIG. 18.

FIGS. 18 and 19 show a configuration related to air feeding tubes and water feeding tubes in the fifth embodiment wherein a air feeding tube and a water feeding tube are disposed also in the tube unit 221. In FIG. 18, an air feeding tube 218A and a water feeding tube 219A are disposed in the control unit 10C, and an air feeding tube 218B and a water feeding tube 219B which are to be connected to the tubes 218A and 219A are disposed in the tube unit 221. An air/water feeding connector 228C which has a nearly conical tapered inside surface having an aperture gradually enlarged toward the outlet is connected to the air feeding tube 218A and the water feeding tube 219A in the receptacle 224, and a similar air/water feeding connector 228D is connected to the air feeding tube 218B and the water feeding tube 219B in the support portion 221A so that an air feeding tube 218 is handled together with a water feeding tube 219.

A second elastic tube member 229 is disposed so as to couple the air/water connectors 228C and 228D with each other. The second elastic tube member 229 is made also of a rubber material, and has a collar-like base 229A, protrusions 229B and 229C which have tapered outer circumferences, and an air feeding tube 218E and a water feeding tube 219E which are formed inside. The base 229A is formed so as to be fitted into the step portion 224A of the receptacle 224, the protrusion 229B is formed so as to be fitted into the air/water feeding connector 228C and the protrusion 229C is formed so as to be fitted into the air/water feeding connector 228D. The base 229A has thickness which is slightly larger than a width of the step portion 224A, and the protrusions 229B and 229C have outer circumferences having diameters which are slightly longer than inside diameters of the air/water feeding connectors 228C and 228D so as to cope with deterioration or contraction of the rubber material.

Further, slits 230 are formed as check valve portions at ends of the air feeding tube 218E and the water feeding tube 219E respectively of the second elastic tube member 229. The slit 230 is formed at a center of the tube, and the check valve is opened with an air pressure or a water pressure and is closed when it is free from a supply pressure. The first and second elastic tube members 227 and 229 may be separate or integral.

For connecting the tube unit 221 to the control section 10C in the fifth embodiment which is configured as described above, the fixing ring 225 is screwed over the receptacle 224 while fitting the first elastic tube member 227 (B, C) into the aspirating connectors 217C and 217D and fitting the second elastic tube member 229 (B, C) into the air/water feeding connectors 228C and 228D. Then, the first and second elastic tube members 227 and 229 serve as coupling tubes (217E, 218E and 219E) which couple the tubes 217A, 218A and 219A with the tubes 217B, 218B and 219B respectively, and function as gaskets which maintain airtightness in the coupled conditions.

A liquid or the like can be aspirated or recovered from a body to be observed through the aspirating tubes 217A and 217B by depressing the aspiration button on the control section 10C, and air and water can be injected to the observation window of the tip section through the air feeding tubes 218A, 218B and the water feeding tubes 219A, 219B by depressing the air/water feeding button. The check valves formed as the slits 230 prevent air or water from flowing backward while it is fed.

The fifth embodiment described above allows the first and second elastic tube members 227 and 229 to be disposable or replace them with new ones at a washing stage. Accordingly, the fifth embodiment makes it sufficient to wash only the aspirating connectors 217C, 217D and the air/water feeding connectors 228C, 228D, thereby providing a merit to facilitate washing. In addition, the first elastic tube member 227 provides a merit that it provides insulation between the aspirating tubes 217A and 217B. Speaking concretely, insulation between the aspirating tubes 217A and 217B provides an advantage as an overall insulating measure for use of radio knives which are inserted as treating implements through the aspirating tubes 217A and 217B.

Sixth Embodiment

Figure 20:
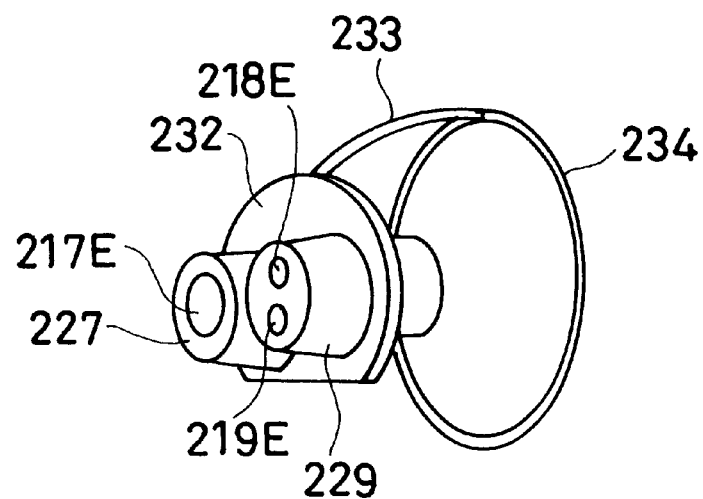
FIG. 20 is a perspective view illustrating a configuration of an elastic tube member used in a sixth embodiment of the present invention.
Figure 21:
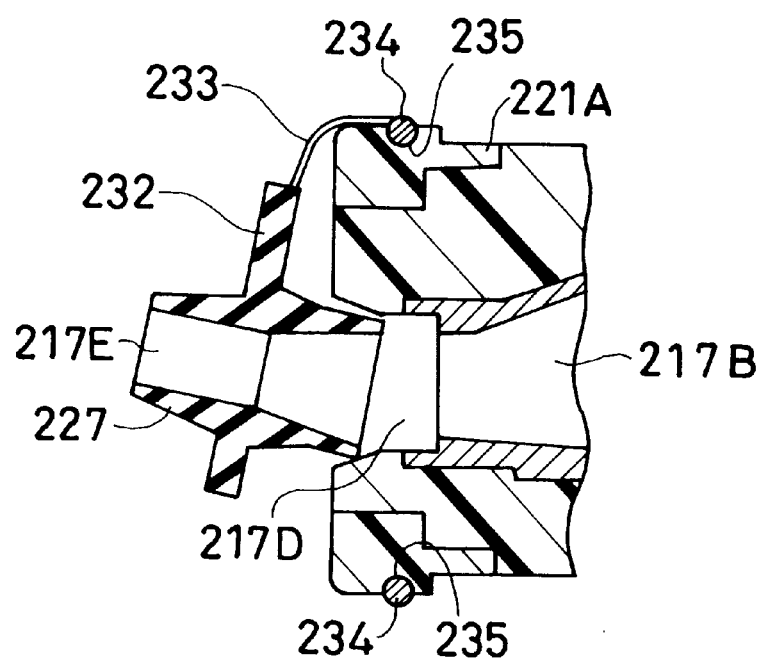
FIG. 21 is a diagram illustrating an aspirating tube on a side of a tube unit in which the elastic tube member shown in FIG. 20 is used.

FIGS. 20 and 21 show a configuration of a sixth embodiment which is related to elastic tube members. In this embodiment, a first elastic tube member 227 and a second elastic tube member 229 are formed integrally with a base 232 as shown in FIG. 20, and a fixing ring 234 made of a rubber material is integrated with the base 232 by way of a thin belt 233. Further, a fitting groove 235 is formed in an outer circumference of a tip of a support portion 221A of a tube unit 221 for fitting the fixing ring 234 as shown in FIG. 21.

The sixth embodiment, as shown in FIG. 21, allows the elastic tube members 227 and 229 to be easily disposed in a coupler by fitting the fixing ring 234 into the fitting groove 235 so as to dispose the first elastic tube member 227 into an aspirating connector 217D (the second elastic tube member 229 can also be disposed into an air/water feeding connector 228D) and facilitates subsequent works for connecting the coupler. Further, the thin belt 233 is torn when the tip of the support portion 221A is fitted into a receptacle 224. Accordingly, the sixth embodiment allows to judge whether or not the elastic tube members 227 and 229 have been used on the basis of a cut condition of the belt 233.

The configuration of the fifth or sixth embodiment which comprises the aspirating tube 217, the air feeding tube 218 and the water feeding tube 219 may be adopted for an endoscope wherein the tubes other than the aspirating tubes are returned to the main unit as in the first embodiment and it is sufficient in such a case to dispose only the first elastic tube member 227.

As apparent from the foregoing description, the fifth and sixth embodiments make it possible to easily maintain airtightness in a condition where the tube unit is connected to the main unit and facilitate to wash airtight structural sections in which bacilli are apt to propagate in particular by making the elastic tube members disposable. Further, merits to facilitate to dispose the elastic tube members and maintain airtightness are obtained by forming protrusions which have tapered surface on the elastic tube members. Furthermore, the back flow preventive means which are formed integrally with the coupling tubes for the elastic tube members eliminate the necessity to dispose back flow preventive means in the tubes of the tube unit and, when the elastic tube members are disposable, it is unnecessary to wash the back flow preventive means which require tedious washing works.

Seventh Embodiment

Figure 22:
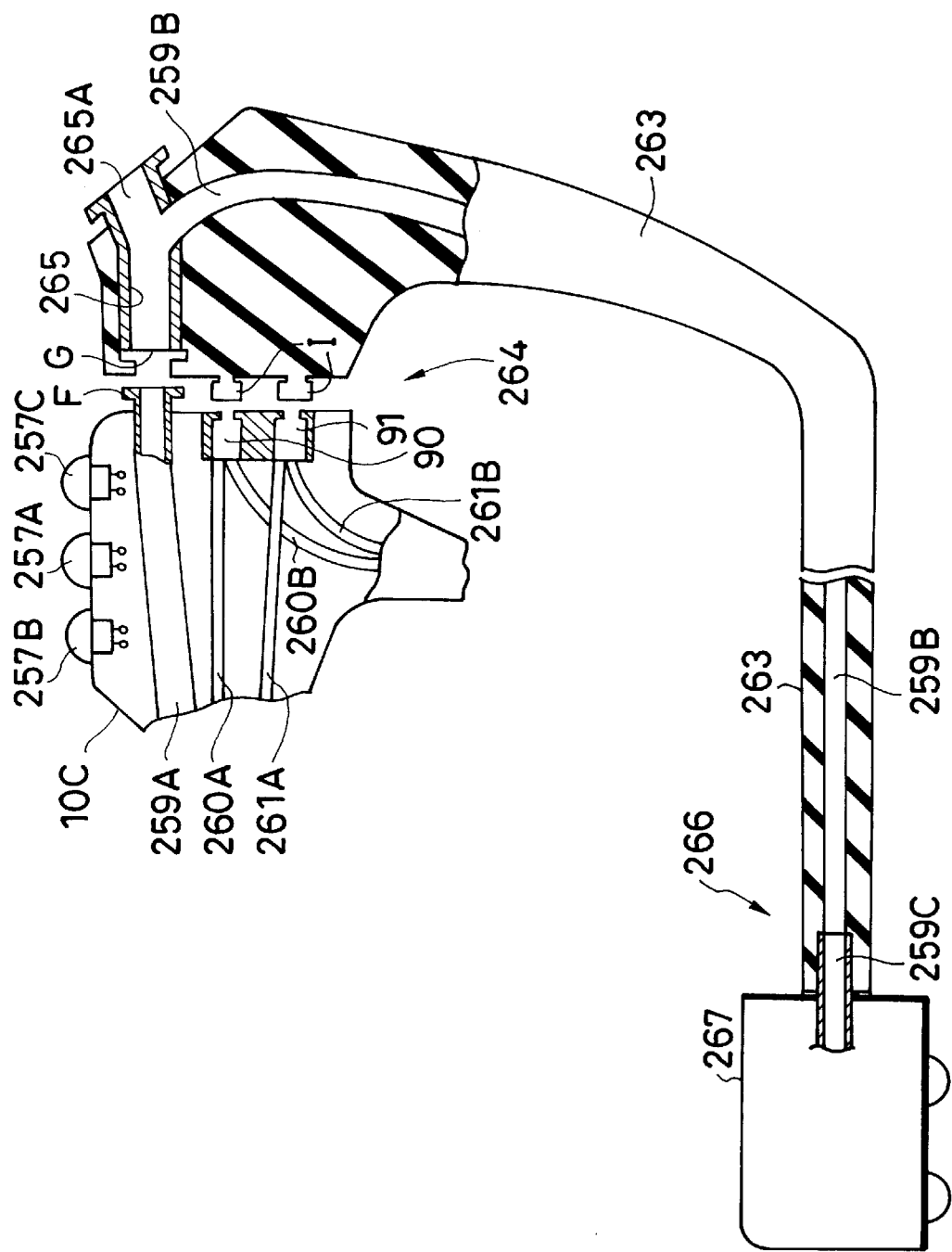
FIG. 22 is a partial sectional view illustrating a configuration of an endoscope preferred as a seventh embodiment of the present invention.

FIG. 22 shows a configuration of a seventh embodiment. In FIG. 22, an aspiration button 257A, an air/water feeding button (two-step switch) 257B and a hard copy button 257C are disposed on a control section 10C, and an aspirating tube 259A which aspirates contents of a body to be observed, a front air feeding tube 260A and a front water feeding tube 261A are disposed in the control section 10C. A flange-like annular convex portion F is formed on a coupler at an end of the aspirating tube 259A. On the other hand, a rear air feeding tube 260B is connected to the air feeding tube 260A by way of a returning section 90 and a rear water feeding tube 261B is connected to the water feeding tube 261A by way of a returning section 91. A ring-like engaging portion protruding inward is disposed in outlet of the returning sections 90 and 91.

A disposable tube unit 263 is detachably coupled with the control section (on a side of a main unit) 10C described above. The tube unit 263 is composed of a control section side support portion and a cable portion which are made of an elastic material such as elastic rubber. An aspirating tube 259B which is to be coupled with the aspirating tube 259A is formed integrally in the tube unit 263. A fitting groove G which is to fit over the annular convex portion F owing to elastic deformation (distortion) of the tube unit is formed in a first coupler 264 of the tube unit 263. Beside the annular groove G, protruding stopper members I are formed so as to be fitted into the returning sections 90 and 91, and grooves are formed, for example, at roots of the stopper members I so that a ring-like engaging portion of the returning sections 90 and 91 are brought into close mesh with the grooves while leaving returning spaces in the returning sections 90 and 91.

Further, a forceps port 265A is formed in the tube unit 263 as a branch of the aspirating tube 259B, and a metal tube 264 is inserted into a portion of the aspirating tube 259B and the forceps port 265A. That is, the aspirating tubes 259A and 259B are used as an introduction port for treating implements, and surroundings of the forceps port 265A require strength of a certain degree. Therefore, a metal tube 265 is laid from the forceps port 265A to the aspirating tube (metal tube) 259A of on the side of the control section 10C.

A rear end of the tube unit 263 is connected to a solenoid valve unit 267 with a second coupler 266 as shown in FIG. 22. Only an aspirating tube 259B is formed in the second coupler 266 of the tube unit 263 and a protruding tube 259C is disposed in the solenoid valve unit 267. Accordingly, the second coupler 266 of the tube unit 263 can be connected simply by elastically deforming and fitting the aspirating tube 259B into the protruding tube 259C.

In the seventh embodiment described above, the tube unit 263 is coupled with the control section 10C by fitting the fitting groove G over the annular convex portion F in the first coupler 264, and fitting the stopper members I into the returning sections 90 and 91. The tube unit 263 is connected to the solenoid valve unit 267 by connecting the aspirating tube 259B to the protruding tube 259C. The control ring used in the other embodiments may be made of a hard resin material and fit over the first coupler 264 described above.

When the tube unit 263 is disposable, the seventh embodiment permits omitting washing and sterilization of the tube unit 263.

What is claimed is:

1. An endoscope having washing ports comprising:

an endoscope main unit which is configured to form openings in the course of tubes disposed in an endoscope, expose these openings outside and allow a washing brush from the openings into front and rear tubes separated by said openings;

an attachment which serves as stoppers for the openings in said main unit or couples tubes with said openings;

front tubes disposed from a tip section to a control section;

rear tubes disposed from said control section to a tube control unit by way of a cable;

openings of said front and rear tubes which are exposably disposed on an outer circumference of said control section;

returning sections which are coupled with the openings of said front and rear tubes and form spaces for returning flow paths; and an attachment which is attachable and detachable to and from the openings or the returning sections in said control unit, maintains said returning sections when attached and exposes the openings of said front and rear tubes as washing ports when detached.

2. A tube structure for the endoscope according to claim 1, wherein an air feeding tube and a water feeding tube are disposed as said front and rear tubes, an aspirating tube which serves also as a treating implement insertion channel is disposed in a tube unit to lead it to a tube control unit along a path separate from said cable and a function of said attachment is imparted to said tube unit.

3. An endoscope according to claim 1, wherein each tube is separated into two branches in said endoscope main unit, an opening is formed in a confluence portion of these two branches as a washing port from which a washing brush can be inserted into the two branch tubes.

4. An endoscope according to claim 1, wherein an aspirating tube which serves also as a treating implement insertion channel is disposed in said endoscope and a forceps port is formed in said attachment so as to communicate with said aspirating tube.

5. An endoscope having washing ports according to claim 1, comprising:

a tube unit which is attachable and detachable to and from said main unit, and has tubes connectable to the tubes disposed on the side of said main unit; and elastic tube members which are interposed between the tubes on the side of said main unit and the tubes on the side of said tube unit, having coupling tubes for coupling said tubes and are made of an elastic material.

6. An endoscope having washing ports according to claim 5, wherein said elastic tube members have protrusions which are inserted or disposed through a base into the tubes on the side of said main unit or the tubes on the side of said tube unit and tapered surfaces which are thinner toward tips thereof are formed on outer circumferences of these protrusions.

7. An endoscope having washing ports according to claim 5, wherein an aspirating tube which serves also as a treating implement insertion channel is disposed in said endoscope and a forceps port is formed in said tube unit so as to communicate with said aspirating tube.

8. An endoscope having washing ports according to claim 1, wherein said tube unit which comprises said aspirating tube is disposed as said attachment and the tube unit having a support portion and a cable portion is made of an elastic material.

9. An endoscope having washing ports comprising:

an endoscope main unit in which openings are formed as washing ports in the course of tubes disposed in an endoscope and exposed outside;

a tube unit which is attachable and detachable to and from said main unit, and has tubes connectable to the tubes disposed on the side of said main unit;

a tube control unit which connects said tube unit and controls switching valves for said tubes;

control switches which are disposed on said tube unit and execute switching operations of said tubes with said tube control unit and wherein first control switches for executing switching operations of said tubes are disposed on said endoscope main unit and second control switches for executing switching operations of said tubes are disposed on said tube unit.

10. An endoscope having washing ports comprising:

an endoscope main unit in which openings are formed in the course of tubes disposed in an endoscope and exposed outside;

a tube unit which is attachable and detachable to and from said main unit, and has tubes connectable to the tubes disposed on the side of said main unit; and elastic tube members which are interposed between the tubes on the side of said main unit and the tubes on the side of said tube unit, having coupling tubes for coupling said tubes and are made of an elastic material;

wherein back flow preventing means are formed integrally with the coupling tubes of said elastic tube members.

11. An endoscope having washing ports comprising:

an endoscope main unit in which openings are formed in the course of tubes disposed in an endoscope and exposed outside;

a tube unit which is attachable and detachable to and from said main unit, and has tubes connectable to the tubes disposed on the side of said main unit; and elastic tube members which are interposed between the tubes on the side of said main unit and the tubes on the side of said tube unit, having coupling tubes for coupling said tubes and are made of an elastic material;

wherein a fixing ring is connected to said elastic tube members and a fitting groove for fitting over said fixing ring is formed in a coupler on the side of said main unit or a coupler on the side of said tube unit.

* * * * *